(12) United States Patent
Liu et al.

(10) Patent No.: US 10,827,937 B2
(45) Date of Patent: Nov. 10, 2020

(54) METHOD FOR NONINVASIVE IMAGING OF CARDIAC ELECTROPHYSIOLOGICAL BASED ON LOW RANK AND SPARSE CONSTRAINTS

(71) Applicant: ZHEJIANG UNIVERSITY, Hangzhou (CN)

(72) Inventors: Huafeng Liu, Hangzhou (CN); Lin Fang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 264 days.

(21) Appl. No.: 15/983,546

(22) Filed: May 18, 2018

(65) Prior Publication Data

US 2019/0209035 A1 Jul. 11, 2019

(30) Foreign Application Priority Data

Jan. 11, 2018 (CN) .......................... 2018 1 0027389

(51) Int. Cl.
| | |
|---|---|
| *A61B 5/00* | (2006.01) |
| *A61B 5/04* | (2006.01) |
| *G06N 7/00* | (2006.01) |
| *G06F 17/14* | (2006.01) |
| *A61B 5/0408* | (2006.01) |
| *A61B 5/05* | (2006.01) |

(52) U.S. Cl.
CPC ........ *A61B 5/04007* (2013.01); *A61B 5/0035* (2013.01); *A61B 5/0044* (2013.01); *A61B 5/04085* (2013.01); *G06F 17/148* (2013.01); *G06N 7/00* (2013.01); *A61B 5/05* (2013.01); *A61B 2562/046* (2013.01); *A61B 2576/023* (2013.01)

(58) Field of Classification Search
CPC ............ A61B 5/04007; A61B 5/04085; A61B 5/0044; A61B 5/0035; A61B 2576/023; A61B 5/05; A61B 2562/046; A61B 5/7225; A61B 5/6804; A61B 5/0402; G06F 17/148; G06N 7/00; G06N 5/003
See application file for complete search history.

(56) References Cited

U.S. PATENT DOCUMENTS 4,961,428 A * 10/1990 Nikias ................ A61B 5/04085
600/512

* cited by examiner

*Primary Examiner* — Scott M. Getzow
(74) *Attorney, Agent, or Firm* — Jiwen Chen; Jacobson Holman PLLC

(57) ABSTRACT

The present invention discloses a method for noninvasive imaging of cardiac electrophysiological based on low rank and sparse constraints. This method decomposes the spatio-temporal distribution of endocardial and epicardial potentials into a low-rank matrix representing smooth potential components and a sparse matrix representing the details of potential salience according to the prior condition of spatio-temporal correlation of the endocardial and epicardial potential distribution of the heart. By introducing low rank and sparse constraints, the solution of the ill-conditioned inverse problem of ECG is constrained to the unique optimal solution. The invention combines the individualized three-dimensional heart model of the subject to obtain a three-dimensional dynamic distribution image of the cardiac endocardial and epicardial potential of the subject, which has important practical application value.

8 Claims, 5 Drawing Sheets

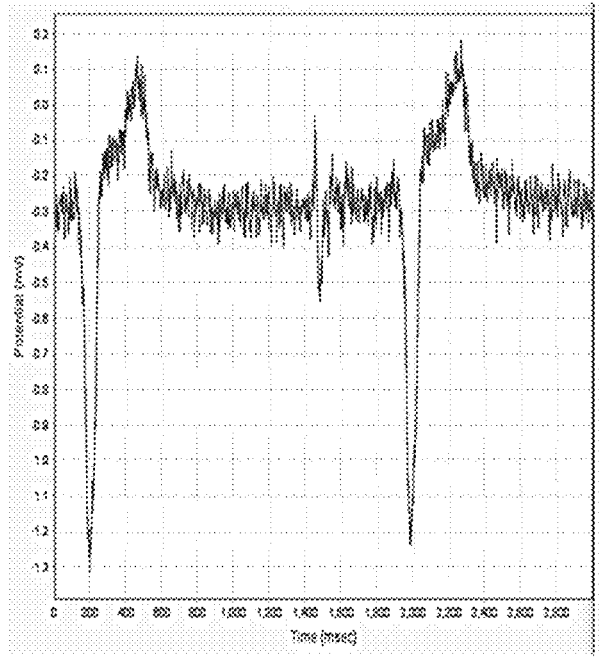
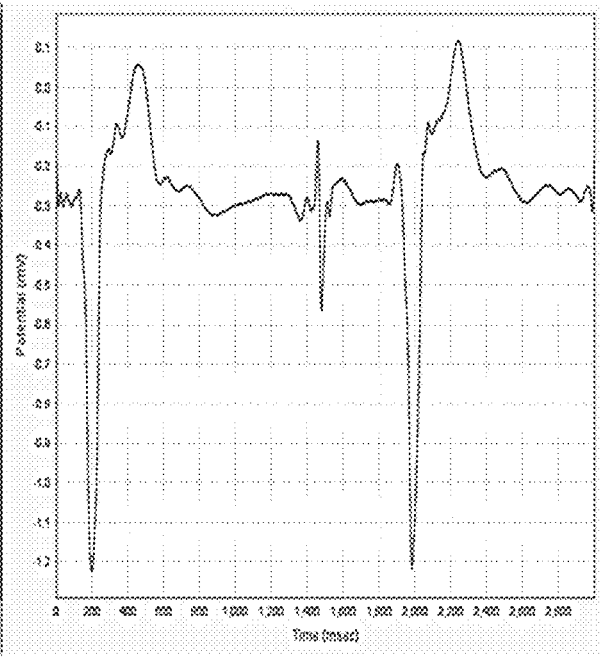
Figure 8 (a)                    Figure 8 (b)
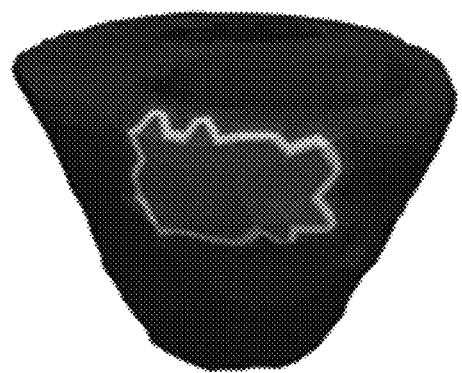
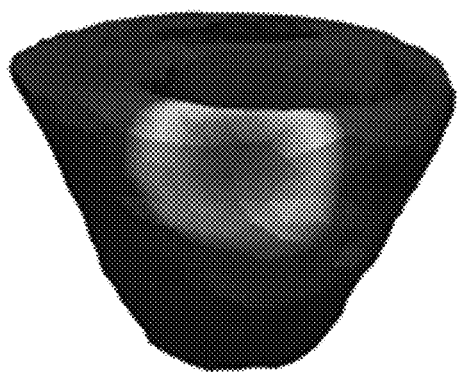
Figure 9 (a)                    Figure 9 (b)

METHOD FOR NONINVASIVE IMAGING OF CARDIAC ELECTROPHYSIOLOGICAL BASED ON LOW RANK AND SPARSE CONSTRAINTS

This application claims the priority benefit of Chinese Application No. 201810027389.7, filed Jan. 11, 2018, which is hereby incorporated by reference.

TECHNICAL FIELD

The present invention belongs to the technical field of cardiac electrophysiological analysis, and in particular relates to a non-invasive cardiac electrophysiological inversion method based on a low-rank sparse constraint.

BACKGROUND OF THE INVENTION

With the continuous development of the medical level, a large number of heart disease diagnosis methods have been proposed and applied to clinical diagnosis, which are mainly divided into intrusive and non-invasive two categories. The most commonly used invasive cardiac electrophysiological imaging techniques include the Ensite system and the CARTO system. Among them, the CARTO system performs 3D electroanatomic mapping of the heart through magnetic field localization technology. The Ensite system detects the intraluminal electric field through the intraluminal electrode and uses the inverse of the Laplace equation to obtain the potential distribution of the heart. The invasive method can provide accurate information about the internal structure and potential of the heart, but there is a certain risk in the subject during the operation.

The most widely used non-invasive method in clinical medicine is electrocardiography. Electrocardiography (ECG) records changes in body surface potential by placing electrodes on the surface of the chest. Then the doctors can infer whether there is abnormality in the electrophysiological activity of the heart by shape, amplitude, and timing of the electrocardiogram waveform. Because of the convenience and safety of electrocardiography, it has become a very important tool in clinical diagnosis. However, there are obvious defects in electrocardiography. The change of body surface potential is only a rough mapping of cardiac electrophysiological activity that doctors can only infer subjectively based on experience, and cannot accurately locate the specific location and shape of the focal point.

In order to improve the accuracy of non-invasive method diagnosis, a series of non-invasive electrophysiological imaging methods based on specific electrophysiological a priori conditions have been generated, which reconstructs the spatial distribution and temporal changes of the endocardial and epicardial potential in the heart by surface potential recording and 3D cardiac models. The Tikhonov regularization method is a classical single parameter method for calculating ill-posed linear inverse problems. The 0-order Tikhonov corresponds to the minimum energy solution estimate, the 1-order Tikhonov corresponds to the smoothest solution estimate, and the second-order Tikhonov corresponds to the most flat solution estimate. In addition, there are truncated singular values, L1 norm, and total variation, which are also used to solve the inverse problem of ECG. However, the above methods are based on a single prior condition (such as the smoothness of the endocardial and epicardial potential) to constrain the solution, and only utilizes the spatial distribution characteristics of the single frame potential signal. However, the lesioned heart has more complex spatial and temporal distribution characteristics, and a single spatial smoothness constraint has certain limitations. Therefore, it is a very significant research issue to explore a more complex prior condition of cardiac electrophysiology and utilize the spatio-temporal distribution characteristics of endocardial and epicardial potential to reconstruct the distribution of the heart potential in accordance with the real situation.

SUMMARY OF THE INVENTION

The present invention provides a method for noninvasive imaging of cardiac electrophysiological based on low rank and sparse constraints. By utilizing the Spatial and temporal correlation of the distribution of ECG, this method decomposes the spatiotemporal distribution image of the endocardial and epicardial potential of the heart into a low-rank matrix representing a smooth background and a sparse matrix representing outstanding details, thereby overcoming the physical morbidity of the inverse problem of the electrocardiogram and constraining the solution to a unique optimal estimate.

A method for noninvasive imaging of cardiac electrophysiological based on low rank and sparse constraints includes the following steps:

(1) collecting body surface potential data (64-lead or more) and thoracic tomography image data;

(2) Based on the thoracic tomographic image data, establishing the three-dimensional torso geometric model and the three-dimensional cardiac geometric model of the study object respectively, then unifying the three-dimensional torso geometry model and the three-dimensional heart geometry model to the same coordinate system to obtain a three-dimensional heart-torso model;

(3) Based on the geometric relationship between the heart and the trunk, establishing a quasi-static electric field model of the heart-trunk and solving the electric field model by using the boundary element method to calculate the positive problem of the ECG. Then getting the mapping relationship between the endocardial and epicardial potential of the heart and body surface potential, that is $\Phi=HU$, where H means transfer matrix, U means endocardial and epicardial potential matrix, $\Phi$ means matrix of body surface potential;

(4) Preprocessing the body surface potential data;

(5) According to the transfer matrix H, establishing a solution to the inverse problem of body surface potential to cardiac potential and introduce low-rank and sparse constraints. Then, inversion of the body surface potential data after pretreatment is performed to solve the inverse problem of the ECG and reconstructing the endocardial and epicardial potential distribution data on the three-dimensional cardiac geometric model.

More specifically, in step (1), the specific operation process of collecting body surface potential data and thoracic tomography image data is as follows: First, making the subject wear a body surface potential recording device with multiple lead electrodes to collect body surface potential data; Then, applying a computerized tomography scan to the subject of the wearing device to obtain the thoracic tomographic image data of the recording electrode position.

More specifically, in step (2), the concrete realization process of my 3D torso geometry model is as follows: First, obtaining the three-dimensional coordinates of each electrode point by electrode point location marked manually of thoracic tomography image, and then performing Delaunay triangulation (or other finite element techniques) on the electrode points in three-dimensional space to obtain The 3D torso geometric model of the study object.

More specifically, in step (2), the concrete realization process of 3D heart geometry model is as follows: First, taking several slices in the short axis direction of the heart by imaging in a thoracic tomography image: downwards include at least apical position and upwards include at least right ventricular outflow tract position. Then, segmenting the slice image in the short axis direction of the heart to obtain the boundary contour of the epicardium, the left endocardium, and the right endocardium respectively. Finally, the above-mentioned series of parallel boundary contours are connected using a triangular mesh, ie, a three-dimensional heart geometric model is obtained.

More specifically, in step (2), considering the unit difference between the digital image space and the physiological space in each orthogonal direction, one needs to unify the 3D torso geometry model and the 3D cardiac geometry model to the same coordinate system. According to the key segment information in the CT image file, the dimensional and spatial position of the 3D cardiac geometry model is corrected. The corrected 3D cardiac geometry model is combined with the 3D torso geometry model to obtain a 3D cardiac-trunk model.

More specifically, in step (3), the specific method for establishing a quasi-static electric field model of the heart-torso is as follows: Assuming that the electric field is a quasi-electrostatic field, the ion flow of myocardial cells provides a field source for the cardiac electric field, and there is no other electric field source in the thoracic cavity besides the myocardium. In the present invention, the heart surface includes the endocardium and the epicardium and is considered as an exiting closed surface. Therefore, a quasi-static electric field model between the heart surface to the torso surface is established as a Laplace equation:

$$\sigma \nabla^2 \varphi(r) = 0$$

Where $\sigma$ means conductivity, $\nabla$ means gradient operator, r means the 3D coordinates of any point in the electric field, $\varphi(r)$ means the electric potential of r.

Since there are no conductors outside the body surface, the derivative of the body surface potential in the direction perpendicular to the body surface outward is 0, and the body surface potential is the potential recorded by the 64-lead electrocardiogram, thereby obtaining the boundary condition:

$$\frac{\partial \varphi(r)}{\partial n} = 0 \text{ on } S_b$$

$$\varphi(r) = \phi(r) \text{ on } S_b$$

$$\varphi(r) = u(r) \text{ on } S_h$$

Where n means the direction perpendicular to the body surface outward, $S_b$ means the body surface, $S_h$ means the heart surface. $\phi(r)$ means the body surface potential data recorded by 64-lead. u(r) means the heart surface (endocardial and epicardial) potential. Then getting the mapping relationship between the endocardial and epicardial potential matrix of the heart and body surface potential matrix, that is $$\Phi = HU$$

where H means transfer matrix, U means endocardial and epicardial potential matrix, $\Phi$ means matrix of body surface potential;

In step (4), the specific method for preprocessing the surface potential data is as follows: First, the body surface potential data is denoised by means of Fourier transform or wavelet transform, and the main information in the potential signal is preserved to eliminate redundant interference. Then, the smoothing is performed on all potential signals denoised in the cardiac cycle to pull the signal baseline horizontally, avoiding the baseline deviation of the different periodic signals and introducing errors.

More specifically, in step (5), the specific method for solving the inverse problem of electrocardiogram is as follows:

First, decomposing the cardiac endocardial and epicardial potential matrix U into a low rank matrix L and a sparse matrix S, representing smooth component and highlight detail of endocardial and epicardial potential respectively, that is U=L+S;

Then, the solution to the inverse problem of establishing the body surface potential to the cardiac potential is as follows:

$$\min_U \{\|L\|_* + \lambda \|S\|_1 + \mu \|HU - \Phi\|_F\}$$

$$\text{s.t.} \quad U = L + S$$

where $\| \|_*$ means nuclear norm, $\| \|_l$ means L1 norm, $\| \|_F$ means Frobenius norm, $\lambda$ and $\mu$ presents weight parameters;

Finally, the above model is optimized by augmented Lagrangian algorithm, and the distribution data of the endocardial and epicardial potential in the three-dimensional heart geometry model is obtained.

The present invention is based on low rank and sparse constrained non-invasive ECG imaging method, and constrains the temporal and spatial distribution of the endocardial and epicardial potential of the heart through two prior conditions of background smoothness and detail sparsity of the ECG, thereby reconstructing an accurate ECG space-time Distribution, through the spatial distribution and timing changes of the potential in the three-dimensional heart model, can accurately and intuitively obtain the location, shape and size of the lesion area, which has important practical value.

BRIEF DESCRIPTION OF THE DRAWINGS

FIG. 8(a) and FIG. 8(b) are schematic diagrams of body surface potential signal waveforms before and after pretreatment, respectively.

FIG. 9(a) is a schematic diagram showing the true result of endocardial and epicardial potential data of the heart.

FIG. 9(*b*) is a schematic diagram of inversion reconstruction results of cardiac endocardial and epicardial potential data.

DESCRIPTION OF THE PREFERRED EMBODIMENTS

In order to more specifically describe the present invention, the technical solutions of the present invention will be described in detail below in conjunction with the accompanying drawings and specific embodiments.

The present invention is based on a low rank and sparse constraint non-invasive ECG imaging method, and the specific implementation steps are as follows:

S1. Collecting the subject's 64-lead ECG and chest CT images.

Figure 1:
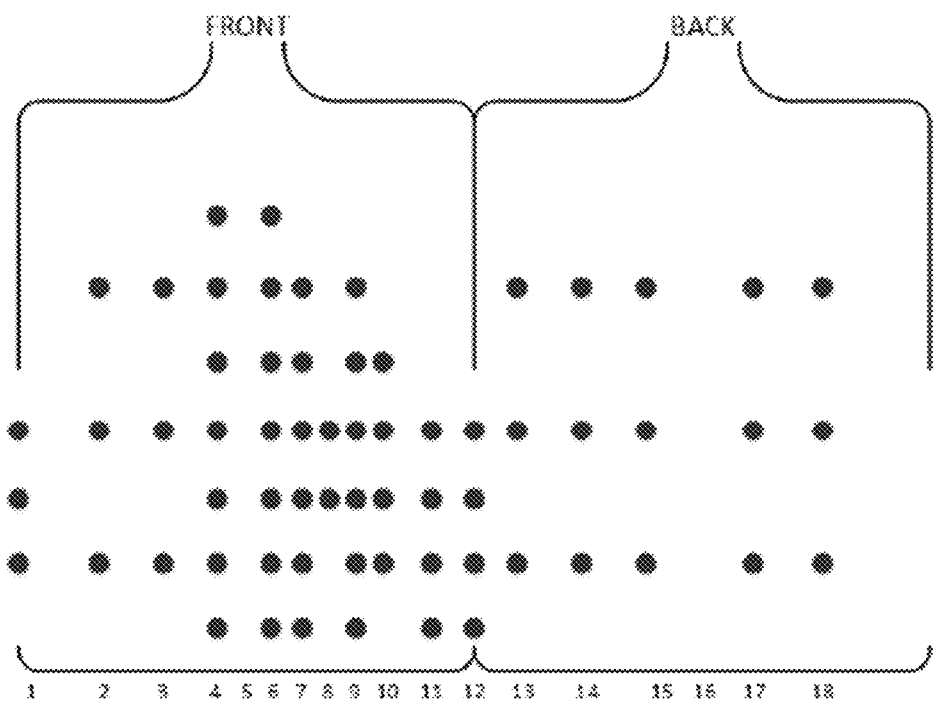
FIG. 1 is a location diagram of the 64-lead electrode on the body surface

First, we let the subject put on a 64-lead vest and collected the subject's 64-lead electrocardiogram to record the surface potential data of multiple cardiac cycles. The distribution of 64 leads on the body surface is shown in FIG. 1. Then, we removed the wire on the vest and retained the detection electrode only. We performed a computed tomography scan of the human chest and acquired enhanced CT image data of the subject's trunk and heart. The subject's personalized torso was recorded with the heart geometry and spatial location.

S2. Creating a personalized three-dimensional heart model.

Figure 2:
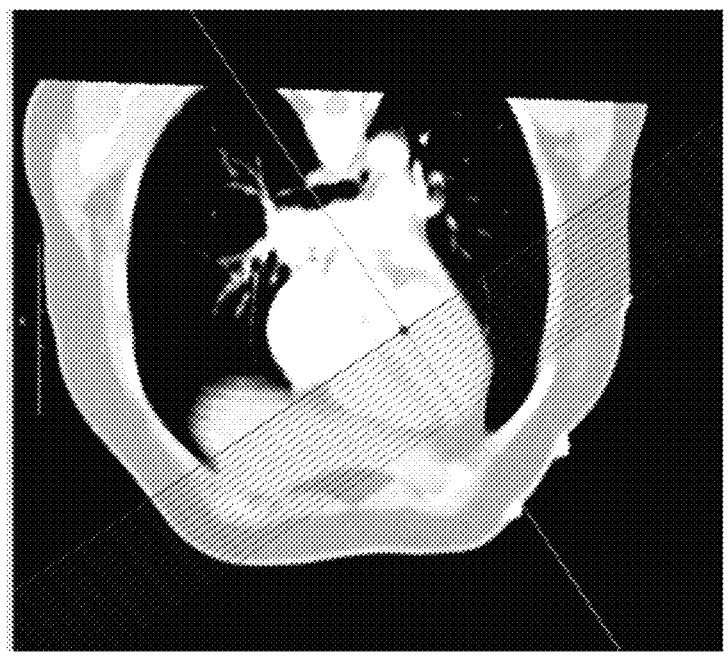
FIG. 2 is a schematic diagram of ventricular slicing in 3D cardiac modeling
Figure 3:
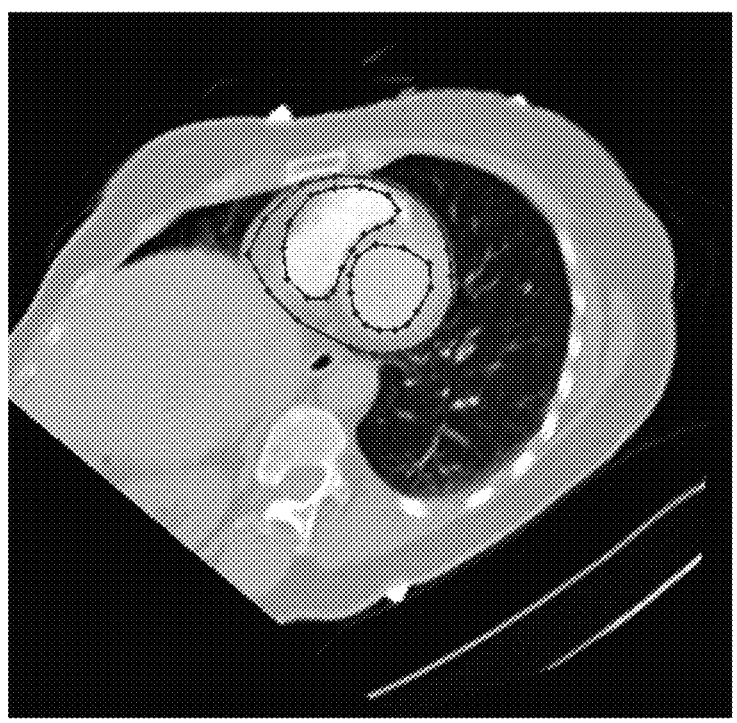
FIG. 3 is a schematic diagram of the outline of the heart
Figure 4:
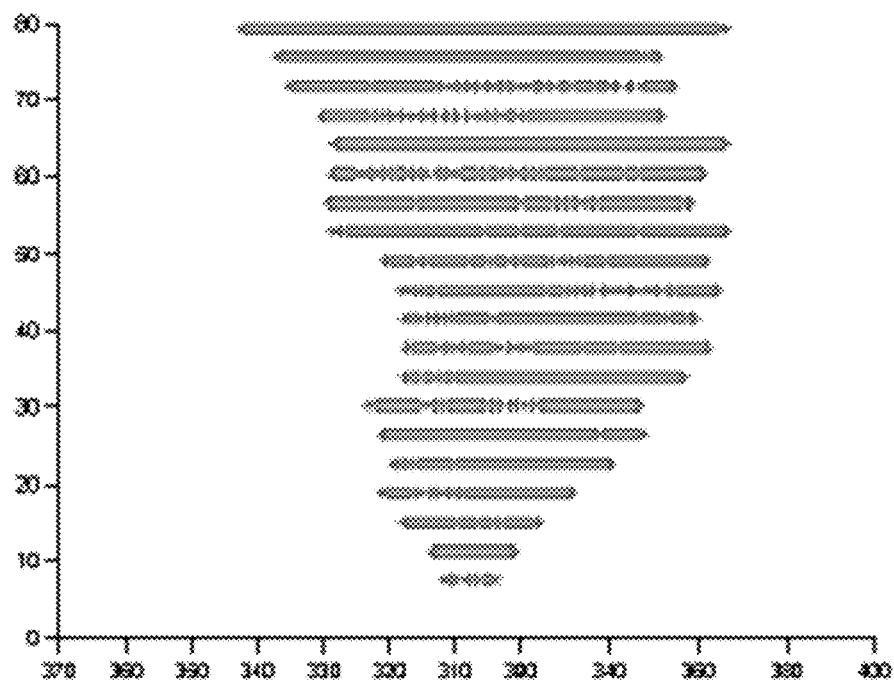
FIG. 4 is a schematic diagram of heart contour data stacking
Figure 5:
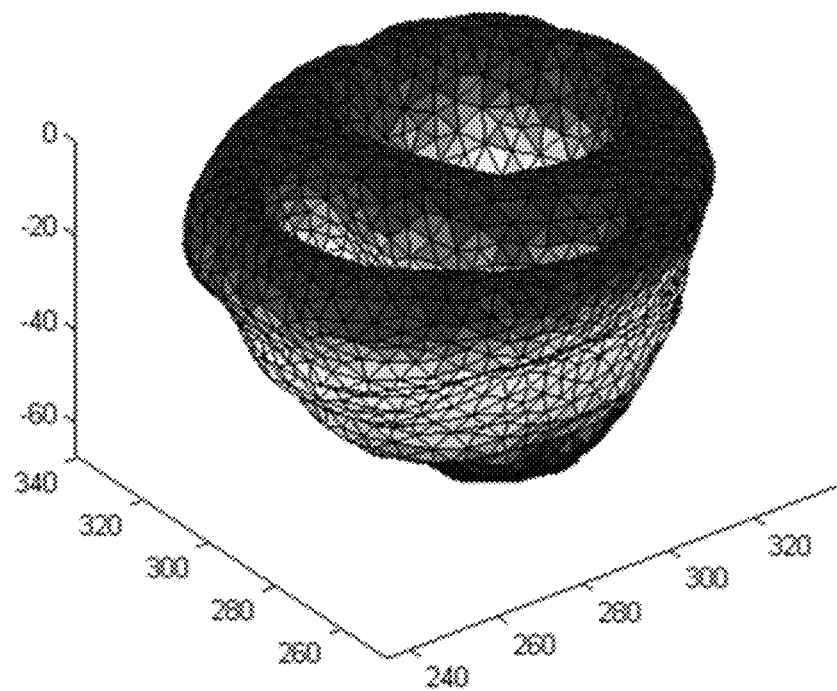
FIG. 5 is a schematic diagram of a three-dimensional heart grid model.

First, from the CT image data of the thorax, we sliced along the short axis of the heart from the top of the ventricle to the apex of the heart, as shown in FIG. 2; then, we extracted the outline of the heart in each slice (the left heart chamber membrane, the right heart chamber membrane, Epicardium), as shown in FIG. 3; then we stacked the heart contour data extracted from all sections, as shown in FIG. 4; finally, we connected the data to the heart contour with the triangle network to obtain a personalized heart three-dimensional grid model as shown in FIG. 5.

S3. Creating a personalized joint heart-torso model.

Figure 6:
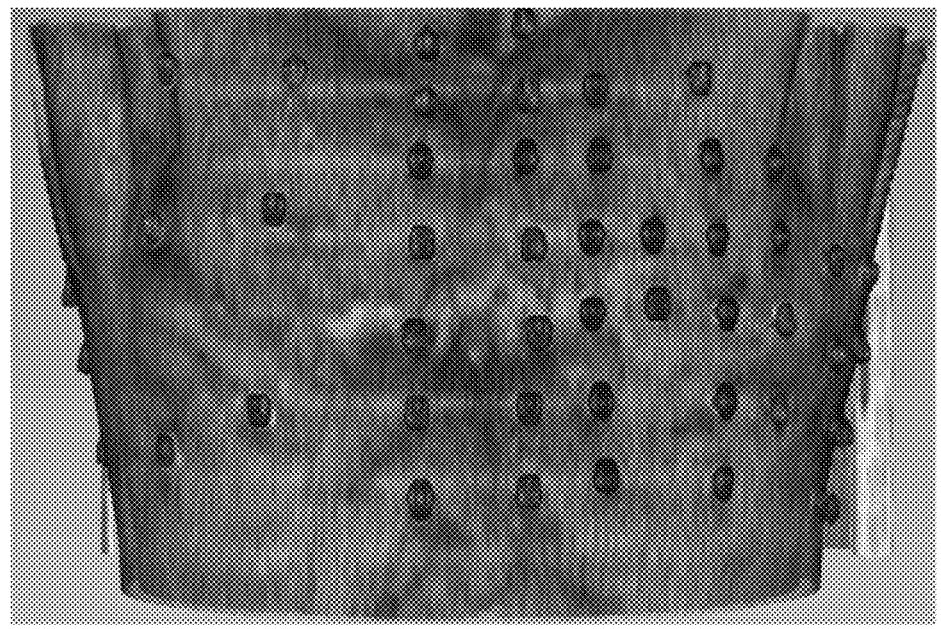
FIG. 6 is a schematic diagram of the 64-lead electrode distribution on the body surface.
Figure 7:
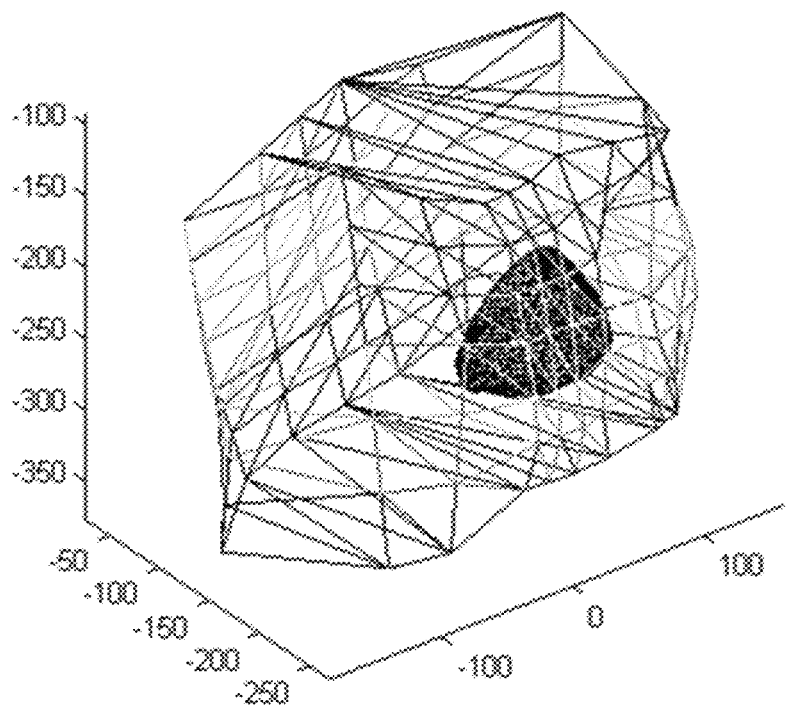
FIG. 7 is a schematic diagram of a heart-torso model in the same coordinate system.

We marked the position of the 64-lead electrocardiogram in the computed tomography data and recorded the three-dimensional coordinates of 64 electrodes. The distribution of the 64-lead electrodes on the human body surface is shown in FIG. 6. The protruding point in FIG. 6 is the detection electrode. Finally, we got a personalized torso three-dimensional model by Delaunay triangulation. The three-dimensional heart model and torso model were calibrated to a unified global coordinate, resulting in a personalized heart-torso model as shown in FIG. 7.

S4. Establishment of quasi-static electric field model of heart-torso.

Assuming that the electric field is a quasi-electrostatic field, the ion flow of myocardial cells provides a field source for the cardiac electric field, and there is no other electric field source in the thoracic cavity besides the myocardium. In the present invention, the heart surface includes the endocardium and the epicardium and is considered as an exiting closed surface. Therefore, a quasi-static electric field model between the heart surface to the torso surface is established as a Laplace equation:

$$\sigma \nabla^2 \varphi(r) = 0$$

Where $\sigma$ means conductivity, $\nabla$ means gradient operator, r means the 3D coordinates of any point in the electric field, $\varphi(r)$ means the electric potential of r.

Since there are no conductors outside the body surface, the derivative of the body surface potential in the direction perpendicular to the body surface outward is 0, and the body surface potential is the potential recorded by the 64-lead electrocardiogram, thereby obtaining the boundary condition:

$$\frac{\partial \varphi(r)}{\partial n} = 0 \text{ on } S_b$$

$$\varphi(r) = \phi(r) \text{ on } S_b$$

$$\varphi(r) = u(r) \text{ on } S_h$$

Where n means the direction perpendicular to the body surface outward, $S_b$ means the body surface, $S_h$ means the heart surface. $\phi(r)$ means the body surface potential data recorded by 64-lead. u(r) means the heart surface potential.

S5. Establishment of mapping relationship between endocardial and epicardial potential of heart and body surface potential.

Using the boundary element method to solve the quasi-static electric field model of the heart-to-torso, the model for transecting the endocardial and epicardial current of the heart through the transfer matrix to the body surface potential can be expressed:

$$\Phi = HU$$

Where $\Phi$ is body surface potential matrix, U is endocardial and epicardial potential matrix, H is transfer matrix and only relates to the heart-torso geometry and conductivity.

S6. Pretreatment of body surface potential data.

First, we used the Fourier transform or wavelet transform to de-noise the 64-lead body surface potential signal, preserved the main information of the signal, removed the redundant interference, then flattened the baseline of ECG signals for all cardiac cycles. In this implementation, wavelet transform was used to filter the body surface potential signal. The frequency threshold is selected from 0.3 to 0.5, and the decomposition level is selected from 7 to 8. The comparison before and after the signal processing is shown in FIG. 8(*a*) and FIG. 8(*b*).

S7. Solving Model of Inverse Problem Based on Low-Rank Sparsity Constraints.

First, we decomposed the endocardial and epicardial potential matrix into a low-rank matrix and a sparse matrix, which represent the smooth background of the endocardial and epicardial potential and highlight the details:

$$U = L + S$$

Where L means the low-rank matrix, S means the sparse matrix.

Then, we forced the L matrix to be a low-rank matrix and the S matrix to be a sparse matrix by iteration, so that the solution to the ill-conditioned inverse problem tends to be optimal. The target expression is as follows:

$$\min \|L\|_* + \lambda \|S\|_1 + \mu \|HU - \Phi\|_F$$
$$\text{s.t. } U = L + S$$

Where $\|L\|_*$ means the nuclear norm of the matrix L, that is the sum of all singular values of the L matrix, and it is the convex relaxation of the matrix rank. $\|S\|_l$ means the L1-norm of the S matrix and the solution to the L1 optimization is a sparse solution; $\|HU - \Phi\|_F$ is a fidelity item which guarantees that the obtained endocardial and epicardial potential has the least error between the positive mapping of the body surface and the actual measured body surface potential; λ and μ are weight parameters.

We used the augmented Lagrangian method to solve the target equation to obtain the best estimate of the endocardial and epicardial potential of the heart:

$$L(L, S, U) = \|L\|_* + \lambda\|S\|_1 - \langle Z, U - (L+S) \rangle + \frac{\beta}{2}\|U - (L+S)\|_F^2 + \frac{\mu}{2}\|HU - \Phi\|_F^2$$

Where Z means Lagrange multiplier, $\langle \ \rangle$ means inner product, λ, β and μ are weight parameters.

Combined with the three-dimensional cardiac model, we obtained a three-dimensional distribution of the endocardial and epicardial potential on the heart, thereby diagnosing the specific location and shape of the corresponding disease and lesion area.

Then we validated the proposed method through experiments, the computer operating environment is: 8G memory, CPU is intel i7, frequency 3.47 GHz; Through the above-mentioned implementation process, the cardiac endocardial and epicardial potential of the myocardial infarction subject is simulated and reconstructed. Under the interference of the Gaussian noise level of 30 dB to 10 dB, the above implementation can restore the position and shape of the infarct scar to different degrees. FIG. 9 shows the reconstruction results with a noise level of 25 dB, where FIG. 9(a) is a true value and FIG. 9(b) is a calculation inversion result. The reconstruction of the endocardial and epicardial potential of subjects with real ventricular premature beats was performed. The inversion of the premature beat point was the same as the position of the premature beat point reconstructed by Ensite3000 by the invasive method.

The foregoing description of the embodiments is provided to facilitate those skilled in the art in understanding and applying the present invention. It will be apparent to those skilled in the art that various modifications to the above described embodiments may be readily made, and that the general principles described herein may be applied to other embodiments without inventive step. Therefore, the present invention is not limited to the above embodiments, and those skilled in the art, based on the disclosure of the present invention, should make improvements and modifications to the present invention within the protection scope of the present invention.

The invention claimed is:

1. A method for noninvasive imaging of cardiac electrophysiology, comprising the following steps:
   (1) recording a subject's surface potential data and thoracic tomography image data;
   (2) based on the thoracic tomographic image data, establishing a 3D torso geometric model of the object and a 3D cardiac geometry model, respectively, then unifying the 3D torso geometry model and the 3D cardiac geometry model into the same coordinate system to obtain a 3D heart-torso model;
   (3) establishing a quasi-static electric field model of the subject's heart-torso based on the geometric relationship between heart and trunk of the subject, wherein the boundary element method is used to solve an electric field model to calculate a positive problem of an electrocardiogram, and a mapping relationship between endocardial and epicardial potential of the heart and body surface potential is obtained as Φ=HU, H is a transfer matrix, U is a cardiac endocardial and epicardial potential matrix, and Φ is a body surface potential matrix;
   (4) pretreating a 64-lead body surface potential data; and
   (5) according to the transfer matrix H, establishing an inverse problem solving model of the body surface potential to the cardiac potential, and then performing an inverse operation of a pre-processed body surface potential data to solve an inverse problem of the electrocardiogram; finally, reconstructing a distribution of cardiac endocardial and epicardial potential in the geometric model of the three-dimensional heart.

2. The method for noninvasive imaging of cardiac electrophysiology according to claim 1, characterized in that: the specific operation process of collecting 64-lead body surface potential data and the thoracic tomographic image data of the study subject of the step (1) is as follows: first, putting the subject on a body surface potential recording device with 64 electrode leads distributed to collect the subject's 64-lead body surface potential data; then subjecting the subject with a wearable device to a computed tomography scan to acquire the thoracic tomographic image data of the recording electrode positions.

3. The method for noninvasive imaging of cardiac electrophysiology according to claim 1, characterized in that: the concrete realization process of establishing a three-dimensional trunk geometric model of the step (2) is as follows: first, manually marking the position of each electrode point in the thoracic tomography image to acquire the three-dimensional coordinates of each electrode point, and then performing triangulation of electrode points in three-dimensional space to obtain a three-dimensional torso geometric model of the study object.

4. The method for noninvasive imaging of cardiac electrophysiology according to claim 1, characterized in that: the concrete realization process of establishing a three-dimensional heart geometric model of the step (2) is as follows: first, intercepting several slices in the direction of the short axis of the heart in the thoracic tomographic image by imaging, and at least the apical position should be included downward, and at least the position of the right ventricular outflow tract should be upward; then, dividing the slices in the short axis direction of the heart to obtain the boundary contours of the epicardium, the left endocardium, and the right endocardium; finally, connecting the above-mentioned series of parallel boundary contours with a triangular mesh, which means, obtaining a three-dimensional heart geometry model.

5. The method for noninvasive imaging of cardiac electrophysiology according to claim 1, characterized in that: unifying 3D geometric model and 3D heart torso geometry model into one coordinate system due to the digital image space and cardiac physiological space in each orthogonal direction difference of the step (2), by concretely correcting the 3D geometric model of heart size and space position basing on the key field information, then fusing corrected 3D geometric model of heart and 3D geometric model of torso to obtain the 3D heart torso model.

6. The method for noninvasive imaging of cardiac electrophysiology according to claim 1, characterized in that: the concrete method for establishing a quasi-static electric field model of the heart and trunk of the step (3) is as follows: assuming that heart electric field is quasi static electric field, the ion circulation of cardiac myocytes provides a field source for the cardiac electric field, there are no other electric field sources in the thoracic cavity except the myocardium; a quasi static electric field model of the heart and trunk is established as follows:

$$\sigma\nabla^2\varphi(r)=-\nabla\cdot(D_i\nabla u(r))$$

where σ means conductivity, ∇ means gradient operator, r means the 3D coordinates of any point in the electric field, φ(r) means the electric potential of r, $D_i$ means electrical conductivity tensor in the myocardium, u(r) means endocardial and epicardial potential of r, ∇·( ) means the divergence of the results in parentheses.

7. The method for noninvasive imaging of cardiac electrophysiology according to claim 1, characterized in that: concrete step for preprocessing of body surface potential data of the step (4) is as follows: first, denoising the body surface potential data by Fourier transform or Wavelet transform, retaining the main information in the potential signal and removing the redundant interference; then, smoothing the signal of all cardiac cycle after denoising, so that the baseline is pulled to a horizontal level, and the error of baseline migration is avoided.

8. The method for noninvasive imaging of cardiac electrophysiology according to claim 1, characterized in that: in step (5), the specific process is as follows:

first, decomposing the cardiac endocardial and epicardial potential matrix U into a matrix L and a matrix S, representing smooth component and highlight detail of endocardial and epicardial potential respectively, that is U=L+S;

then, the solution to the inverse problem of establishing the body surface potential to the cardiac potential is as follows:

$$\min_U\{\|L\|_* + \lambda\|S\|_1 + \mu\|HU-\Phi\|_F\}$$
$$\text{s.t. } U = L+S$$

where $\|\ \|_*$ means nuclear norm, $\|\ \|_l$ means L1 norm, $\|\ \|_F$ means Frobenius norm, λ and μ presents weight parameters;

finally, the above model is optimized by augmented Lagrangian algorithm, and the distribution data of the endocardial and epicardial potential in the three-dimensional heart geometry model is obtained.

* * * * *